(12) United States Patent
Lee et al.

(10) Patent No.: US 8,075,585 B2
(45) Date of Patent: Dec. 13, 2011

(54) DEVICE AND METHOD FOR TREATMENT OF A VASCULAR DEFECT

(75) Inventors: Elaine Lee, Sunnyvale, CA (US); Robert Abrams, Los Gatos, CA (US)

(73) Assignees: Stryker Corporation, Kalamazoo, MI (US); Stryker NV Operations Limited, Dublin (IE)

(*) Notice: Subject to any disclaimer, the term of this patent is extended or adjusted under 35 U.S.C. 154(b) by 614 days.

(21) Appl. No.: 10/231,391

(22) Filed: Aug. 29, 2002

(65) Prior Publication Data

US 2004/0087998 A1   May 6, 2004

(51) Int. Cl.
 *A61M 29/00*   (2006.01)
(52) U.S. Cl. ...................................................... 606/200
(58) Field of Classification Search .................. 606/200, 606/213, 151, 155, 157, 158, 215; 128/830, 128/831, 833, 840, 841
See application file for complete search history.

(56) References Cited

U.S. PATENT DOCUMENTS

| | | | |
|---|---|---|---|
| 4,530,840 A | 7/1985 | Tice et al. | 514/179 |
| 4,767,628 A | 8/1988 | Hutchinson | 424/426 |
| 4,891,225 A | 1/1990 | Langer et al. | 424/428 |
| 4,906,474 A | 3/1990 | Langer et al. | 424/428 |
| 5,056,211 A | 10/1991 | Hauser | 29/527.2 |
| 5,108,420 A * | 4/1992 | Marks | 606/213 |
| 5,122,136 A | 6/1992 | Guglielmi et al. | 606/32 |
| 5,145,935 A | 9/1992 | Hayashi | 528/65 |
| 5,234,520 A | 8/1993 | McClintock | 156/218 |
| 5,354,295 A | 10/1994 | Guglielmi et al. | 606/32 |
| 5,506,300 A | 4/1996 | Ward et al. | 525/88 |
| 5,540,680 A | 7/1996 | Guglielmi et al. | 606/32 |
| 5,665,822 A | 9/1997 | Bitler et al. | 525/92 |
| 5,750,585 A | 5/1998 | Park | 521/143 |
| 5,855,578 A | 1/1999 | Guglielmi et al. | 606/32 |
| 5,895,385 A | 4/1999 | Guglielmi et al. | 606/32 |
| 5,904,703 A * | 5/1999 | Gilson | 606/213 |
| 5,925,037 A | 7/1999 | Guglielmi et al. | 606/32 |
| 5,935,148 A | 8/1999 | Villar et al. | 606/213 |
| 5,941,249 A | 8/1999 | Maynard | 128/898 |
| 5,944,714 A | 8/1999 | Guglielmi et al. | 606/32 |
| 5,947,963 A | 9/1999 | Guglielmi | 606/32 |
| 5,976,126 A | 11/1999 | Guglielmi et al. | 606/32 |
| 6,010,498 A | 1/2000 | Guglielmi | 606/32 |
| 6,036,720 A | 3/2000 | Abrams et al. | 606/213 |
| 6,063,070 A | 5/2000 | Eder | 606/1 |
| 6,063,104 A | 5/2000 | Villar et al. | 606/213 |
| 6,066,133 A | 5/2000 | Guglielmi et al. | 606/32 |
| 6,083,220 A | 7/2000 | Guglielmi et al. | 606/32 |

(Continued)

FOREIGN PATENT DOCUMENTS

WO   99 05977 A   2/1999

(Continued)

*Primary Examiner* — Gary Jackson
*Assistant Examiner* — Katherine Dowe
(74) *Attorney, Agent, or Firm* — Vista IP Law Group LLP (57) ABSTRACT

A device for the occlusion of a vascular defect includes a first sheet and a second sheet which may be formed from a material which is the same as or different from the first sheet. At least one sheet functions as a securement member, and at least one sheet functions as an occluding member. The first sheet may be replaced by an alternative securement structure. At least one sheet may be coated with a biocompatible material for promoting integration with the vasculature and/or healing of the vascular defect.

17 Claims, 4 Drawing Sheets

U.S. PATENT DOCUMENTS

| | | | | |
|---|---|---|---|---|
| 6,139,564 | A * | 10/2000 | Teoh | 606/213 |
| 6,168,622 | B1 | 1/2001 | Mazzocchi | 623/1.2 |
| 6,193,748 | B1 | 2/2001 | Thompson et al. | 623/1.3 |
| 6,251,116 | B1 * | 6/2001 | Shennib et al. | 606/155 |
| 6,284,802 | B1 | 9/2001 | Bissett et al. | 514/739 |
| 6,309,367 | B1 | 10/2001 | Boock | 602/1 |
| 6,335,029 | B1 | 1/2002 | Kamath | 424/423 |
| 6,368,586 | B1 | 4/2002 | Jacob et al. | 424/78.08 |
| 6,388,043 | B1 | 5/2002 | Langer et al. | 528/80 |
| 6,409,749 | B1 | 6/2002 | Maynard | 623/1.1 |
| 6,413,536 | B1 | 7/2002 | Gibson et al. | 424/423 |
| 6,551,303 | B1 * | 4/2003 | Van Tassel et al. | 604/508 |
| 6,596,013 | B2 * | 7/2003 | Yang et al. | 606/215 |
| 6,605,111 | B2 * | 8/2003 | Bose et al. | 623/1.18 |
| 6,613,074 | B1 * | 9/2003 | Mitelberg et al. | 623/1.11 |
| 6,689,150 | B1 * | 2/2004 | VanTassel et al. | 606/200 |
| 6,746,468 | B1 * | 6/2004 | Sepetka et al. | 606/200 |
| 6,749,622 | B2 * | 6/2004 | McGuckin et al. | 606/213 |
| 6,802,851 | B2 * | 10/2004 | Jones et al. | 606/200 |
| 6,860,899 | B1 * | 3/2005 | Rivelli, Jr. | 623/1.22 |
| 7,288,105 | B2 * | 10/2007 | Oman et al. | 606/215 |
| 2003/0093108 | A1 * | 5/2003 | Avellanet et al. | 606/194 |
| 2006/0206143 | A1 * | 9/2006 | West | 606/200 |

FOREIGN PATENT DOCUMENTS

WO      01 30267 A      5/2001

* cited by examiner

DEVICE AND METHOD FOR TREATMENT OF A VASCULAR DEFECT

BACKGROUND OF THE INVENTION

Many minimally invasive or noninvasive interventional medical devices and procedures have been used to treat defects in the vasculature which are not easily reached by surgical procedures. Such medical devices which are adapted for implantation in body lumens in order to support weakened or occluded vessel walls and allow fluid flow are well known and commercially available. One such device is a vascular stent, for example. Stents may be employed to prop up vessel walls and maintain openings in vessels in the coronary system, the brain, the urinary, biliary, esophageal, tracheal and bronchial tracts, and so forth.

However, in some situations, it is desirable to block fluid flow. For example, one serious defect in the vascular system is an aneurysm which is an area of a weakened vessel wall that causes a bulge or bubble to protrude from the adjacent vessel. If untreated, an aneurysm may continue expanding until it bursts, causing hemorrhage. It is therefore often desirable to block fluid flow to the aneurysm.

Devices used for the treatment of such defects may be referred to as vaso-occlusive devices and are commonly deployed to the aneurysm site through the use of a catheter device. Vaso-occlusive devices can have a variety of configurations, and are generally formed of one or more elements that have a deployed configuration for blocking blood flow which is different from their configuration during delivery to the site.

Probably the most widely used method of treating aneurysms endovascularly is coil embolization. However, while this method is very effective for aneurysms having a smaller neck size, it is not as easily used for wide-necked or giant aneurysms because it is more difficult to fill the aneurysm sac adequately and/or to maintain the stability of the coils inside the sac.

Devices for bridging the necks of wide-necked or narrow-necked aneurysms are found, for example, in U.S. Pat. Nos. 5,935,148, 6,063,070, 6,036,720, 6,063,104 and U.S. Pat. No. 6,139,564. These devices may also be used to stabilize the placement of vaso-occlusive devices such as helically wound coils, i.e. coil embolization methods, in the aneurysm or may be used to, at least partially, close the aneurysm neck. The aneurysm neck bridge or retainer assemblies described in the patents above may be delivered to the aneurysm in a variety of different ways, but preferably are attached to an electrolytically severable joint for their deployment. After deployment of the neck bridge or retainer, the aneurysm is at least partially filled with a vaso-occlusive device such as a helically wound coil. The vaso-occlusive devices may also be delivered to the aneurysm using a number of different methods such as by a core wire which is linked to the coils by an electrolytically severable joint or a mechanically severable joint. The vaso-occlusive devices may also be simply pushed into the aneurysm. The success of such devices as those described above may depend on several factors, however, including whether or not the device can migrate out of the aneurysm through the neck of the aneurysm.

Another example of a vaso-occlusive device applicable to the treatment of an aneurysm is a covered stent or a stent-graft. Some covered stents have a limited usefulness due to the stiffness of the device, and synthetic grafts themselves have a tendency to occlude when employed in small blood vessels. Arteries where there is an aneurysm typically have a lot of branching, and when employing a covered stent, there is a further risk of occluding the small branch vessels arising from the parent artery rather than simply blocking the neck of the aneurysm as desired.

Thus, it would be beneficial to have a vaso-occlusive device that can be delivered to an aneurysm or other body vessel in a primary unexpanded configuration, wherein such device can be deployed and released to assume a secondary, expanded configuration which occludes the neck of the aneurysm, and which can be anchored at the site of the aneurysm so that it does not migrate from the site.

SUMMARY OF THE INVENTION

The present invention relates to an improved device and method for the treatment of large, wide-necked aneurysms.

In one aspect, the present invention relates to a device for the treatment of a defect in a vessel of a patient wherein the defect is in the form of a sac and the sac further has a neck portion. The device includes at least one sheet for occluding the defect from the vessel, and at least one securement member. At least one of the sheet or the securement member is within the sac and at least one of the sheet or the securement member is within the vessel, but both are not in the sac or in the vessel.

In one embodiment the securement member is within the sac and includes a plurality of struts and the sheet is in the vessel and substantially occludes the defect from the vessel.

In another aspect, the present invention relates to a device for the occlusion of a vascular defect which includes a two-leaf or two-sheet structure including a first sheet and a second sheet which may be formed from a material which is the same as or different from the first sheet. At least one sheet functions as a securement member, and at least one sheet functions as an occluding member. The first sheet and/or the second sheet may act to occlude the vascular defect and the first and/or second sheet may also act to anchor and stabilize the vaso-occlusive device at the neck of the vascular defect. The first sheet and the second sheet may be formed of the same material, or may be formed of different materials. The first sheet or the second sheet may be replaced by an alternative securement member according to the present invention.

The first sheet may include a first surface which interfaces with the vasculature and a second opposing non-interfacing surface and the second sheet may also include a first surface which interfaces with the vasculature and a second opposing non-interfacing surface. It may be desirable to coat, imbed, or mix in the material from which the sheet is formed, a third material which promotes integration of the device with the vasculature and/or which promotes healing of the aneurysm. The interfacing surface may be desirably coated, for example, with such a material.

The first sheet and the second sheet further have a first unexpanded configuration for delivery of the vaso-occlusive device through the vasculature to the site of the aneurysm, and a second expanded configuration in which the first sheet occludes the vascular defect from the parent vessel, and the second sheet anchors the first sheet inside of, and at the neck of the vascular defect. Desirably, the vaso-occlusive device is delivered to the site of the vascular defect through the use of a catheter delivery device. A retractable sheath may also be employed.

Alternatively, the second sheet may occlude the vascular defect while the first sheet functions as an anchor.

The vaso-occlusive device may be further positioned inside the vascular defect and at the neck of the vascular defect through the use of any means known to those of skill in the art such as a pusher wire. The vaso-occlusive device may be detachably connected using severable junctions, for example, to the pusher wire using any detachable connection known in the art. Severable junctions can be severed using a number of different mechanisms including, but not limited to, electrolytic corrosion, mechanical actuation, hydraulic pressure, thermal processes, electromagnetic energy, and so forth.

The first sheet or second sheet may be optionally replaced with another anchoring system such as struts. In this embodiment, it is particularly desirable to include a biocompatible material on the interfacing surface of the first sheet to promote integration with the vasculature and/or healing of the vascular defect.

The first and second sheet may be connected prior to delivery through the patient's vasculature, or they may be connected in situ.

In any embodiments, the sheet may further include a material which promotes integration of the device with the vasculature such as a biocompatible adhesive, a material which promotes healing, a material which promotes fibrosis, a material which promotes endothelialization, a material which promotes tissue growth, or some mixture thereof.

The present invention further relates to a method of treating a vascular defect including the steps of deploying the vaso-occlusive device to the site of the vascular defect, inserting the first sheet or other anchoring means through the neck of the vascular defect, deploying the first sheet, and deploying the second sheet or other anchoring means on the opposing side of the neck of the vascular defect. Suitably, both the first sheet and the second sheet are deployed through the use of a catheter delivery device. A retractable sheath may optionally be employed. If the first sheet or the second sheet are replaced with another anchoring means, then the anchoring means is also suitably deployed through the use of a catheter delivery device. A retractable sheath may be optionally employed. Deployment may be carried out with one device, or a combination of devices if the sheets are connected in situ, for example.

The device may be employed in minimally invasive, interventional procedures for the treatment of a vascular defect where it is desirable to block the flow of fluid, if not completely then to a substantial degree, into the defective area of the vessel.

These and other aspects and advantages of the invention will become apparent from the following detailed description and the accompanying drawings, which illustrate by way of example the features of the invention.

DETAILED DESCRIPTIONS OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

Figure 1:
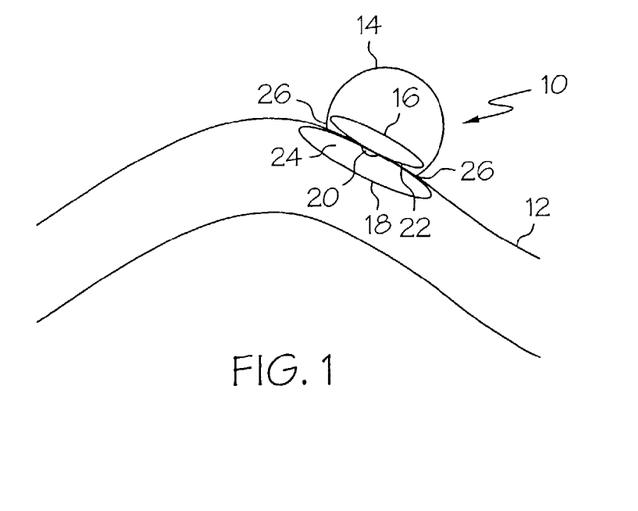
FIG. 1 illustrates a two-leaf vaso-occlusive device according to the present invention in a deployed state at the site of a vascular defect.

Turning now to the figures, FIG. 1 shows generally at 10, a two-leaf or two-sheet vaso-occlusive device, according to the present invention, hereinafter referred to as sheets. The vaso-occlusive device is shown positioned inside a blood vessel 12 at the site of a vascular defect, in this case, a side-wall aneurysm 14. Device 10 is shown having a first sheet 16 in an expanded state inside of the aneurysm 14 and a second sheet 18 connected to the first sheet 16 by a connector 20. First sheet 16 has a vessel interface surface 22 and an opposing, non-interface surface and second sheet 18 has a vessel interface surface 24 and an opposing non-interface surface. The first sheet 16 may be connected to the second sheet 18 prior to deployment in the vessel and may thus be deployed in a single catheter device, or first sheet 16 and second sheet 18 may be deployed separately, and connected inside the vessel.

Further, either interface surface 22 of sheet 16, interface surface 24 of sheet 18, or both, may optionally be coated with, embedded with, or the material itself mixed with, a biocompatible material to promote integration of the device with the vessel, or to promote healing, or the like. This may include biocompatible materials which promote adhesion, fibrosis, tissue growth, endothelialization or cell growth, and so on and so forth.

Examples of biocompatible polymeric materials include, but are not limited to, proteins such as collagen, fibrin, fibronectin, antibodies, cytokines, growth factors, enzymes, and so forth; polysaccharides such as heparin, chondroitin; biologically originated crosslinked gelatins; hyaluronic acid; poly($\alpha$-hydroxy acids); RNA; DNA; polyesters and polyorthoesters such as polyglycolides, polylactides and polylactide-co-glycolides; polylactones including polycaprolactones; polydioxanones; polyamino acids such as polylysine; polycyanoacrylates; poly(phosphazines); poly(phosphoesters); polyesteramides; polyacetals; polyketals; polycarbonates and polyorthocarbonates including trimethylene carbonates; degradable polyethylenes; polyalkylene oxalates; polyalkylene succinates; chitin; chitosan; oxidized cellulose; polyhydroxyalkanoates including polyhydroxybutyrates, polyhydroxyvalerates and copolymers thereof; polymers and copolymers of polyethylene oxide; acrylic terminate polyethylene oxide; polyamides; polyethylenes; polyacrylonitriles; polyphosphazenes; polyanhydrides formed from dicarboxylic acid monomers including unsaturated polyanhydrides, poly(amide anhydrides), poly(amide-ester) anhydrides, aliphatic-aromatic homopolyanhydrides, aromatic polyanhydrides, poly(ester anhydrides), fatty acid based polyanhydrides, and so forth; other biocompatible or naturally occurring polymeric materials; and so forth; copolymers and terpolymers thereof; fragments of biologically active materials; and mixtures thereof. Hereinafter, the term copolymer shall be used to refer to any polymer having two or more monomers.

Some biocompatible polymers are also considered bioabsorbable such as polylactides, polyglycolides, polylactide-co-glycolides, polyanhydrides, poly-p-dioxanones, trimethylene carbonates, polycaprolactones, polyhydroxyalkanoates, and so forth.

Biocompatible polymers which are not biodegradable which find utility herein include, but are not limited to, polyacrylates; ethylene-vinyl acetates; cellulose and cellulose derivatives including cellulose acetate butyrate and cellulose acetate propionate; acyl substituted cellulose acetates and derivatives thereof; non-erodible polyolefins; polystyrenes; polyvinyl chlorides; polyvinyl fluorides; polyvinyl (imidazoles); chlorosulphonated polyolefins; polyethylene oxides; polyethylene glycols; polyvinyl pyrrolidones; polyurethanes; polysiloxanes; copolymers and terpolymers thereof; and mixtures thereof.

Some examples of various polymers described above are found in U.S. Pat. No. 4,891,225 and U.S. Pat. No. 4,906,474 (polyanhydrides), U.S. Pat. No. 4,767,628 (polylactides, polylactide-co-glycolic acid), U.S. Pat. No. 4,530,840 (polylactides, polyglycolides, and copolymers thereof), U.S. Pat. No. 5,234,520 (biodegradable polymers), and so forth. Each of these patents is incorporated by reference herein in its entirety.

Some of these biocompatible polymers are described in U.S. Pat. No. 6,413,536 which is also incorporated by reference herein in its entirety.

See also commonly assigned U.S. Pat. No. 6,335,029 which is incorporated by reference herein in its entirety.

One of ordinary skill in the art would understand that such biodegradable polymers are by far too numerous to list here. Thus, this list is not exhaustive and is intended for illustrative purposes only.

Suitable non-polymeric materials include, for example, hormones and antineoplastic agents.

Examples of other biocompatible materials which promote integration with the vasculature of the patient include, for example, processed human or animal tissue including, for example, cells or cell fragments, engineered vascular tissue, matrix material from bladder, stomach, liver, genetic material of a natural or synthetic origin, and so forth.

Figure 2:
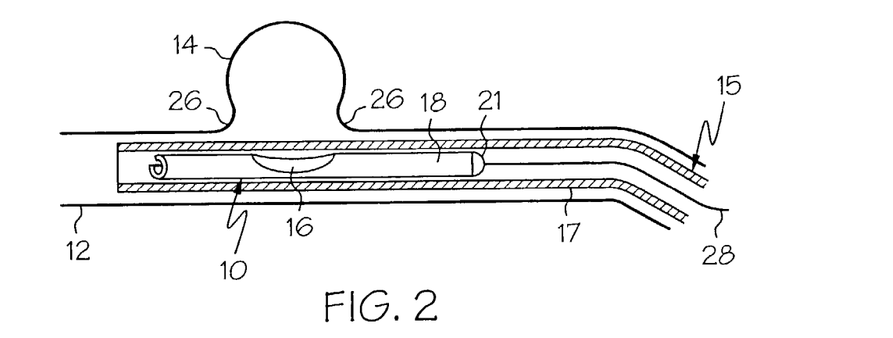
FIG. 2 illustrates a device according to the present invention in an unexpanded state in combination with a catheter delivery device.
Figure 3:
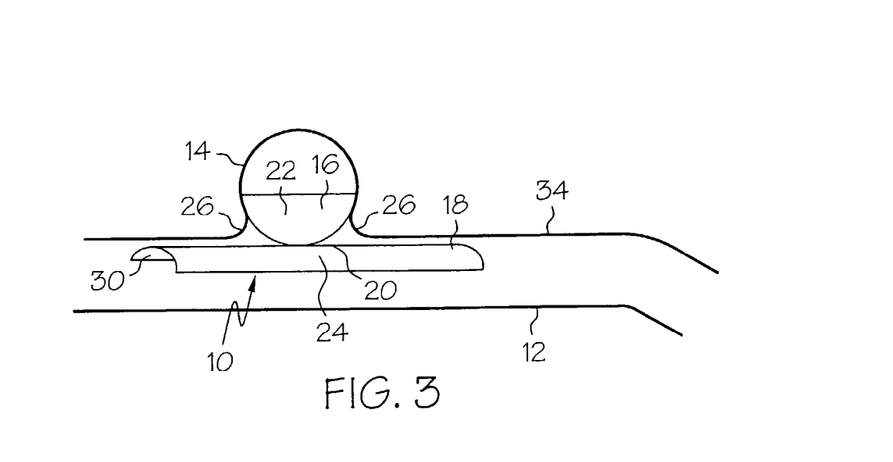
FIG. 3 illustrates an embodiment of a vaso-occlusive device according to the present invention in a deployed state at the site of a vascular defect.

FIGS. 2-3 illustrate deployment of a vaso-occlusive device 10 according to the present invention having a two-sheet structure into a side wall aneurysm 14. As shown in FIG. 2, vaso-occlusive device 10 is delivered through vessel 12 in a collapsed configuration inside the shaft 17 of a catheter delivery device 15. The catheter delivery device 15 is used to position vaso-occlusive device 10 such that sheet 16 and sheet 18 of vaso-occlusive device 10 are approximately centered at the neck 26 of aneurysm 14. Sheet 16 and sheet 18 of vaso-occlusive device 10 are shown in their unexpanded state inside the catheter delivery device 15 in FIG. 2. In this embodiment, the second sheet, in its unexpanded state, is in a rolled form. The sheets may also be folded, for example. A pusher wire 28 for pushing the first sheet 16 from the catheter and into the aneurysm and the second sheet 18 from the catheter is also shown.

FIG. 3 illustrates the vaso-occlusive device 10 of FIG. 2 after deployment and expanded at the aneurysm 14. At this point, the catheter delivery device 15 has been pulled back such that sheet 16 and sheet 18 are deployed. As catheter delivery device 15 is pulled back, sheet 16 is first deployed, and as catheter delivery device is pulled back further, sheet 18 is then released. Optionally, a retractable sheath may be employed. FIG. 3 shows both sheet 16 and sheet 18 in their fully deployed, expanded state. In this embodiment sheet 18 is shown in the form of a rectangular sheet which is convex to the vessel wall 34 on which the vascular defect 14 is located. Sheet 18 is also convex to the aneurysm neck 26. The interfacing surface 24 of sheet 18 may include a biocompatible material for promoting integration of the device with the patient's vasculature or more rapid healing of the aneurysm. A portion of the opposing non-interfacing surface 30 is clearly shown in FIG. 3. Further, the interfacing surface 22 of sheet 16 may also optionally include a biocompatible material for promoting integration of the device with the patient's vasculature or more rapid healing of the aneurysm.

The first sheet, in this embodiment, is functioning primarily as a securement member to keep the device in position, while the second sheet is functioning primarily as the occlusion member. In other embodiments, the shape of the first sheet may be designed to occlude the defect, and the second sheet designed to function as a securement member, or both sheets may be shaped to function as both occluding members and as securement members.

Figure 4:
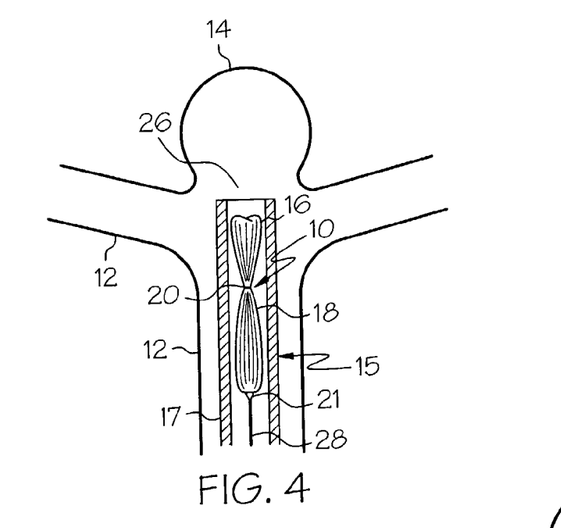
FIG. 4 illustrates an alternative embodiment of a device according to the present invention in an unexpanded state inside a catheter delivery device.
Figure 5:
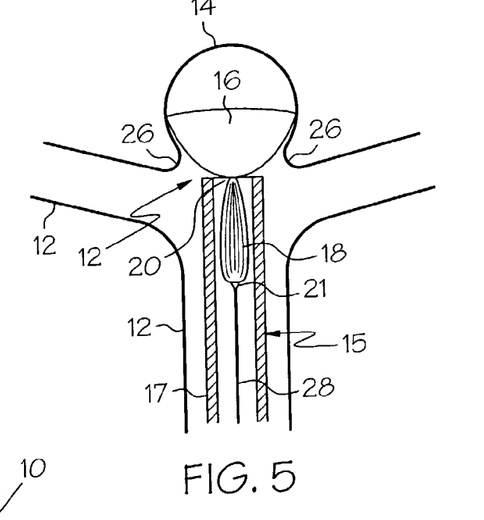
FIG. 5 illustrates the same device as in FIG. 4 in a partially deployed state at the site of a vascular defect.
Figure 6:
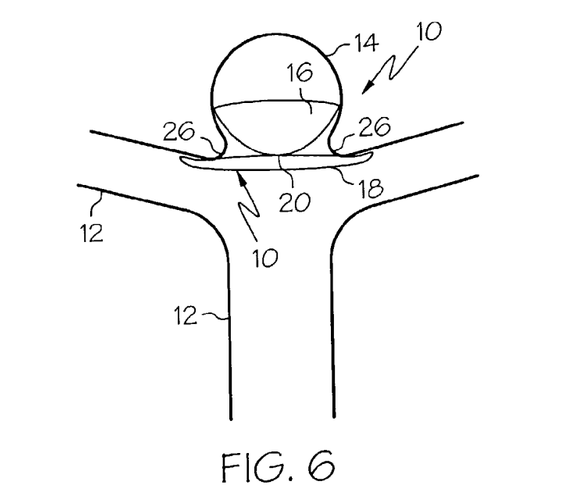
FIG. 6 illustrates the device of FIGS. 4 and 5 in a fully deployed and expanded state.

FIGS. 4-6 illustrate deployment of a vaso-occlusive device 10 according to the present invention in which the vaso-occlusive device 10 is employed in a terminal aneurysm 14. As shown in FIG. 4, vaso-occlusive device having a first sheet 16 and a second sheet 18 is delivered through vessel 12 via a catheter delivery system 15 to the site of the aneurysm 14. FIG. 4 illustrates the vaso-occlusive device in which sheet 16 and sheet 18 are both inside catheter shaft 17 in an unexpanded state. Sheet 16 and sheet 18 are attached via connector 20. In this example, the sheets are in a folded rather than a rolled configuration in their unexpanded states. A pusher wire 28 is shown removably attached to vaso-occlusive device 10. Removable detachment may be accomplished through a variety of means, including, for example, severable junctions such as those severable by electrolytic corrosion, mechanical actuation, hydraulic pressure, thermal processes, electromagnetic energy, and so forth. This list is intended for illustrative purposes only, and is not exhaustive of what attachment systems may be employed in the present invention. One of ordinary skill in the art knows such attachment systems.

FIG. 5 illustrates the same vaso-occlusive device 10 as shown in FIG. 4 in a now partially deployed state in which first sheet 16, shown in an umbrella form, has been deployed inside aneurysm 14 and has been positioned at neck 26 of aneurysm 14. Pusher wire 28 is employed to push sheet 16 into the aneurysm, and may then be used to pull sheet 16 back until it is in contact with neck 26. Sheet 18 is still in an undeployed, unexpanded state inside of catheter shaft 17. Sheet 18 is connected to the first sheet 16 by a connector 20.

The operator may then continue to use pusher wire 28 to push sheet 18 outside of catheter shaft 17 while catheter deliver device 15 is then pulled back (not shown).

FIG. 6 illustrates vaso-occlusive device 10 in a fully deployed state wherein both sheet 16 and sheet 18 are in position at neck 26 of aneurysm 14 and sheet 18 has also been deployed.

It is important to note that the sheets do not have to be in any particular shape or configuration so long as the shape of at least one of the sheets provides adequate occlusion of the vascular defect such that a substantial amount of the blood flow is blocked and so long as at least one of the sheets provides adequate securement of the device at the neck of the vascular defect. Some examples of shapes include, but are not limited to, umbrella like structures, parabolic structures, spheres, discs, rectangular structures or semicircular partial cylinders which bend convexly toward the vascular defect, and the like. Furthermore, the sheet may be in the form of a rectangle which forms a semi-folded convex structure when deployed. The convex side is toward the neck of the vascular defect.

Figure 7:
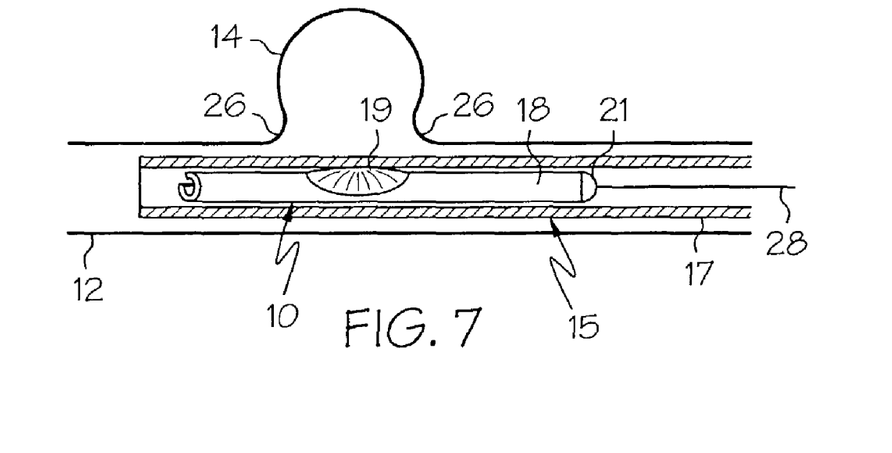
FIG. 7 illustrates an alternative embodiment of the device according to the present invention in an unexpanded state within a catheter delivery device.

FIG. 7 illustrates an alternative embodiment in which sheet 16 has been replaced with struts 19 for anchoring the vaso-occlusive device in position at the site of the vascular defect 14. In this depiction, the vaso-occlusive device 10 is shown in an unexpanded state inside the shaft 17 of catheter delivery device 15. Struts 19 are collapsed over sheet 18 which in this embodiment is shown in a rolled configuration in its unexpanded configuration. Pusher wire 28 can be seen detachably connected at 21 using a severable junction which can be severed using a number of different mechanisms including, but not limited to, electrolytic corrosion, mechanical actuation, hydraulic pressure, thermal processes, electromagnetic energy, and so forth. It is thus at this junction 21 that the vaso-occlusive device 10 is eventually detached from pusher wire 28 which is disposed inside catheter shaft 17 of catheter delivery device 15. A retractable sheath may be optionally employed. Other methods of detachment not described herein, but known in the art, may also be employed in detaching the device of the present invention. Severable junctions which may be employed in the present invention are described, for example, in U.S. Pat. Nos. 5,122,136, 5,354,295, 5,540,680, 5,855,578, 5,895,385, 5,925,037, 5,944,714, 5,947,963, 5,976,126, 6,010,498, 6,066,133 and U.S. Pat. No. 6,083,220, each of which is incorporated by reference herein in its entirety.

Figure 8:
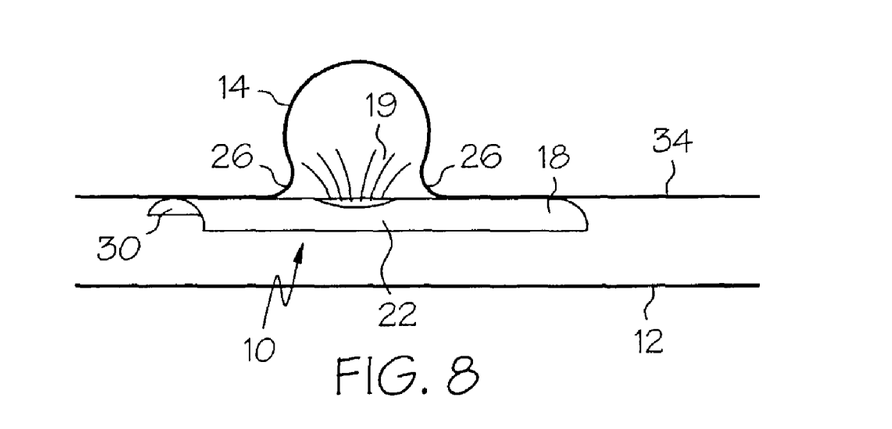
FIG. 8 illustrates the same device as in FIG. 7 in a deployed, expanded state at the site of a vascular defect.

FIG. 8 illustrates the same device as in FIG. 7 in a deployed, expanded state at the site of the vascular defect 14. In this embodiment, the interfacing surface 22 of sheet 18 has a coating of a biocompatible material for promoting integration of the device with the vasculature. Sheet 18 is shown convex to the neck 26 of vascular defect 14 and to vessel wall 34 on which the vascular defect is found and thus the interfacing surface 22 is in close contact with the vessel wall 34 and the neck 26 of vascular defect 14. The non-interfacing surface 30 can be clearly seen in this embodiment. The device has been detached from pusher wire 28.

Figure 9:
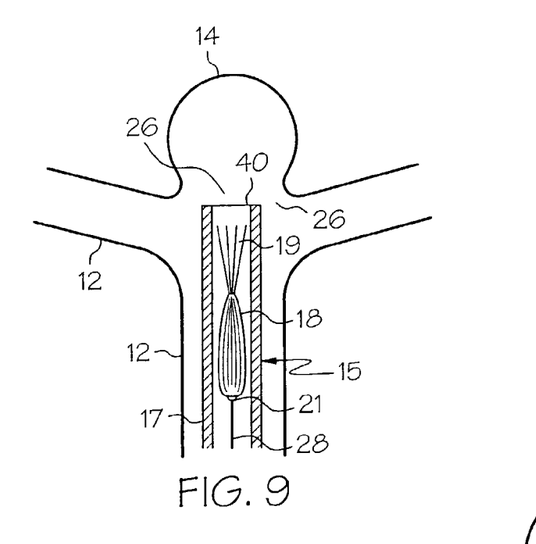
FIG. 9 illustrates a device similar to that shown in FIGS. 7 and 8 being deployed to a terminal vascular defect inside a catheter delivery device.

FIG. 9 illustrates an alternative embodiment in which sheet 16 again has been replaced by anchoring struts 19. This particular device is being employed at the site of a terminal aneurysm rather than a side wall aneurysm as in FIGS. 7 and 8. Again, in FIG. 9, the device is shown in a collapsed configuration inside of the shaft 17 of a catheter delivery device 15. A retractable sheath may be optionally employed. Struts 19 are shown at the distal end 40 of catheter 15 so that the struts are pushed into the vascular defect 14 first and are deployed first as well.

Figure 10:
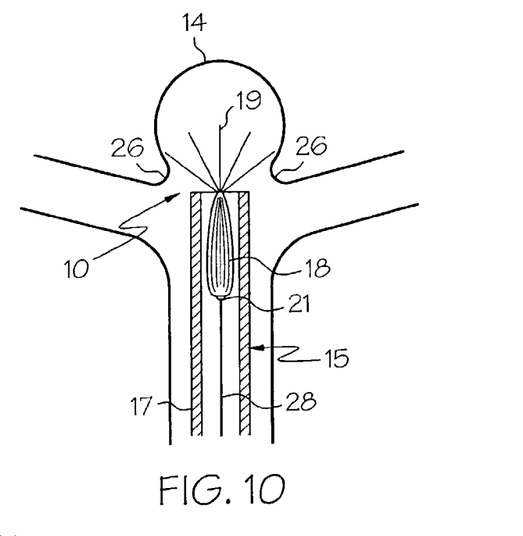
FIG. 10 illustrates the same device as in FIG. 9 in a partially deployed state.

FIG. 10 shows the struts 19 deployed inside the vascular defect 14 while sheet 18 is still collapsed inside the shaft 17 of catheter delivery device 15. In both FIGS. 9 and 10, the vaso-occlusive device 10 is shown connected to pusher wire 28 at 21.

Figure 11:
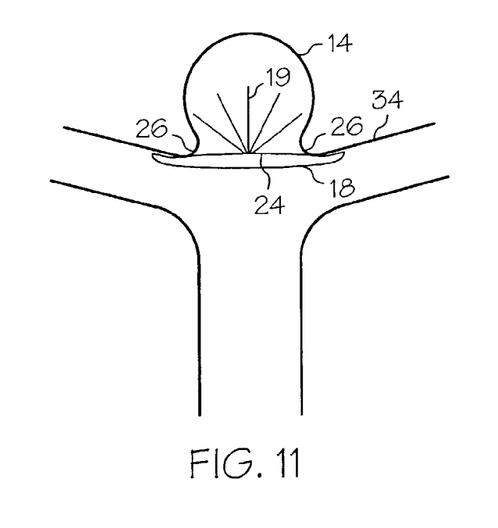
FIG. 11 illustrates the same device as in FIGS. 9 and 10 in a fully deployed, expanded state.

In FIG. 11, the sheet has now been deployed, the catheter delivery device has been pulled back, the pusher wire detached and the device is anchored at the neck 26 of aneurysm 14. In this embodiment, sheet 18 is not shown convex to the vessel wall 34 and aneurysm neck 26 as the embodiment shown in FIG. 8.

The sheets may be constructed from any of a variety of materials including, but not limited to, polymeric material. Biocompatible, bioresorbable and biodegradable materials are suitable. Of course, materials may have any combination of those properties or all of those properties, as well.

Examples of useful polymeric materials include both synthetic and natural materials. Further, the materials may be biocompatible and/or biodegradable materials. Examples of useful polymer materials include, but are not limited to, polyolefins including polyethylene and polypropylene, polyesters such as polyethyleneterephthalate (PET) and polybutylene terephthalate (PBT), polyurethanes, acrylics, polypeptides, polyethers, polyamides, fluoropolymers such as expanded polytetrafluoroethylene, and so on and so forth.

Swellable polymeric materials find utility herein. Such materials include those which are known to expand and become lubricious in aqueous fluids including, for example, a class of materials referred to generally as hydrogels may also be employed in the manufacture of the device according to the present invention. Such materials include hydrophilic, macroporous, polymeric, hydrogel foam material. Examples of such materials include, but are not limited, polyvinylpyrrolindone, polyethylene oxide and its copolymers with polypropylene oxide, polyacrylic acids, polyvinyl alcohols, hyaluronic acid, heparin, chondroitin sulfate, pectinic acid, carboxyl-derivatized polysaccharides, polyhydroxy ethyl methacrylate, polyacrylamide, hydrolyzed polyacrylonitriles, polymethacrylic acid, polyethylene amines, polysaccharides, and copolymers and combinations thereof, and so forth.

One particular example of a swellable material includes a swellable foam matrix formed as a macroporous solid is described in U.S. Pat. No. 5,750,585 which is incorporated by reference herein in its entirety. This material includes a foam stabilizing agent and a polymer or copolymer of a free radical polymerizable hydrophilic olefin monomer crosslinked with up to about 10% by weight of a multiolefin-functional cross-linking agent.

Naturally based materials or those which are biologically derived which find utility herein include, but are not limited to, collagen foams, harvested vascular material, films constructed from processed tissues, and so forth.

Suitable bioresorbable materials include, but are not limited to, degradable hydrogels, lactides/glycolides or PHAs. More specific examples of suitable bioresorable materials include, but are not limited to, collagen, polycaprolactone, poly(glycolic acid), poly(3-hydroxybutric acid), poly(dl-lactic acid), poly(1-lactic acid), poly(dl-lactide/glycolide) 50:50, poly(hydroxyvalerate), poly(hydroxyvalerate-hydroxybutyrate), or other PHAs. Such materials are described in U.S. Pat. No. 5,056,211 and U.S. Pat. No. 6,251,116, both of which are incorporated by reference herein in their entirety.

Non resorbable polymers and elastomers such as silicones, polyolefins, fluoropolymers, or polyurethanes might also be used.

Shape memory materials are suitable for use in formation of the vaso-occlusive device of the present invention. Shape memory materials may be polymeric or metallic. Shape memory materials have the ability to remember their original shape, either after mechanical deformation, or by cooling and heating. Such materials are said to undergo a structural phase transformation. Typically, shape memory polymers (SMPs) are found to be segregated linear block co-polymers having a hard segment and a soft segment wherein the hard segment is crystalline, with a defined melting point, and the soft segment is amorphous, with a defined glass transition temperature. However, the hard segment may be amorphous and have a glass transition temperature rather than a melting point, and the soft segment may be crystalline and have a melting point rather than a glass transition temperature. The melting point or glass transition temperature of the soft segment is substantially less than the melting point or glass transition temperature of the hard segment. Some examples of shape memory polymers include, but are not limited to, those formed from polyethers, polyacrylates, polyamides, polysiloxanes, polyurethanes, polyether amides, polyurethane/ureas, polyether esters, urethane/butadiene copolymers, polynorbornenes, and mixtures thereof. See, for example, U.S. Pat. Nos. 5,506, 300, 5,145,935, 5,665,822, and U.S. Pat. No. 6,388,043 each of which is incorporated by reference herein in its entirety. Degradable shape memory polymers may also be employed.

Shape memory metals suitable for use herein include the alloys of TiNi (NITINOL®), CuZnAl, and FeNiAl, for example. These materials undergo a structure phase transformation referred to as a martensitic transformation.

In some situations, where a shape memory metal is employed, for example, it may be appropriate to employ a metal mesh construction having appropriate geometrical features and cross patterns to provide adequate flexibility. Such metal meshes may be constructed from Nitinol®, for example, which is a super elastic nickel titanium alloy. Furthermore, with such a configuration, stainless steel, may also be used. This type of configuration may be more appropriate for an embodiment in which the first sheet is employed as a securement member for the second sheet, which functions as an occluding member for the vascular defect. The first sheet may then be appropriately constructed of the metal mesh configuration.

It is also possible to employ metals for other configurations. When using a metal substructure, it may be desirable to coat it with a biocompatible, polymeric, biodegradable, or bioabsorbable material. Furthermore, the coating may have all of those characteristics. When the device is comprised of metal or includes metal components the metal must be sufficiently flexible to provide the desired degree of flexibility in the vessels it is used in. As noted above, the geometric pattern of the metal within the device may be important to obtaining preferred results and may be a sinusoidal or circular metal substructure.

Compressed foams may also be employed in the present invention because they have the ability to return to their original shape. Both open and closed cell foams may be employed. Materials satisfactory for use in compressed foams include, but are not limited to medical grade silicones and polyurethanes. As described above, natural materials such as collagens, may also be employed to make a compressed foam material.

Copolymers, and crosslinkable versions of the above described materials may also be suitable for use herein. And, of course, mixtures of the various materials described above may also be employed in the manufacture of the device according to the present invention.

Each sheet may be constructed of the same material, or they may be constructed of different materials or blends of materials.

The sheets may be of a uniform thickness, or the thickness of the sheet may be varied over the surface of the sheet. For example, the sheets may be formed such that they are thinner at the edges.

If the first sheet is replaced by a securement member such as one having a plurality of struts, the struts may be formed from a metal or metal alloy as well.

As described above, it is desirable to incorporate either into the sheet material itself, or on the surface of the sheet, a biocompatible material which promotes integration with the vasculature or healing such as biocompatible adhesives, polymeric materials, tissue, cells, genetic material, and so forth.

The desirable compound or drug may be added to the sheet or sheets using a variety of methods including coating the sheet(s), embedding the compounds or drugs into the material from which the sheet(s) is constructed, mixing the compounds or drugs in the material prior to formation of the sheet(s), and so forth.

A biocompatible adhesive may be added on the surface which is capable of forming a bond at the aneurysm neck, either on the inside of the aneurysm, if the device is delivered and deployed inside the aneurysm or vascular defect, or to the outside of the aneurysm neck, if it is delivered and deployed inside the parent vessel but outside of the aneurysm. Such biocompatible adhesives are described in U.S. Pat. No. 6,368, 586 incorporated by reference herein in its entirety.

As noted above, such compounds or drugs may promote a variety of activities in the body, including, for example, tissue growth or endothelialization. In the latter instance, the some or all of the surfaces of the sheet, in particular the surface which interfaces with the vasculature, may be lined or coated with endothelial cells. These cells may be cells extracted from the patient the device is being placed in or from a tissue culture of such cells from another patient.

Other useful compounds include the polysaccharides such as heparin, for example, which can be beneficially used alone or in combination with hydrogels or hydrophilic compounds, for example.

Anticoagulants compound may be extremely useful as a coating on devices inserted into the vessels of the cardiovascular system. Compounds such as Taxol® may be a useful compound for coating or embedding within materials of a device of the invention.

Other useful materials which may be incorporated into the device include, but are not limited to, antiplatelet agents, calcium agonists, antiinflammatory compounds, antiproleferative drugs, hypolipidemic agents, and angiogenic factors. The device may be comprised such that all or any of these compounds are coated or embedded on the surface of the material, or mixed in the material.

The material from which the vaso-occlusive device is formed or the vaso-occlusive device itself may be modified, or provided with other additives as well, to make the vaso-occlusive device visible by conventional imaging techniques. For example, the device may be rendered visible using fluoroscopic techniques, rendered MRI visible, or both. This can be accomplished through the use of markers such as wire windings, marker bands, rivets, plugs, and so forth, or the radiopaque or MRI visible materials may be incorporated into the material from which the vaso-occlusive device is formed. Any suitable radiopaque or MRI visible material may be employed.

Suitable materials for providing radiopacity to the device include but are not limited to, platinum, rhodium, palladium, rhenium, iridium, tantalum, tungsten, gold, silver, alloys of these metals, as well as polymeric materials with barium, for example. Radiopacity is desirable for visualization of the device for purposes of positioning the device at the site of the defect and to position the device inside the defect and for proper anchoring of the device.

The above lists of materials are intended for illustrative purposes only and are by no means exhaustive. There is a vast array of materials which may be employed in the device of the present invention for a variety of purposes. One of ordinary skill in the art knows of such materials.

The invention is also directed to the vaso-occlusive device of the present invention in combination with a catheter delivery device. Various constructions of catheter delivery devices are known in the art and as such any suitable construction may be employed herein. A retractable sheath may be optionally employed.

The invention is further directed to a method of occluding a vascular defect having an opening. The method comprises the steps of:
a) deploying a first sheet having an unexpanded configuration and an expanded configuration, as discussed above, through the neck of a vascular defect and into the vascular defect;
b) expanding the first sheet in the vascular defect;
c) deploying a second sheet having an expanded configuration and an unexpanded configuration, as discussed above, on the outside of the vascular defect, the second sheet being attached to the first sheet; and
d) expanding the second sheet.

The sheets may be connected prior to delivery to the site, or they may be connected in situ.

The first sheet or the second sheet may be replaced with an alternative securement structure. In one embodiment, the securement structure includes a plurality of struts.

The invention may be used to close and substantially occlude an opening of an aneurysm from a parent blood vessel.

The above disclosure is intended for illustrative purposes only and is not exhaustive. The embodiments described therein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A device for the occlusion of a defect in the vasculature, the defect having a neck portion, said device comprising:
a first sheet formed from a first shape memory material and having an unexpanded and an expanded configuration, said unexpanded configuration being in the form of a rolled, elongate cylindrical shape having a longitudinal axis; and
a second sheet formed from a second shape memory material which is the same as or different from said first material and having an unexpanded configuration in which said second sheet is conformed onto the surface of said rolled cylindrical shape of said unexpanded first sheet, and an expanded configuration formed when the shape memory material exceeds its transition temperature such that said second sheet expands transversely outward from the longitudinal axis of said first sheet to form one of an umbrella-like shape or a semi-spherical shape, said first sheet and said second sheet are connected by a separable connector, said second sheet is inside the defect and said first sheet is outside the defect, each of said first sheet and said second sheet shaped to function as an occlusion member which blocks the flow of fluid to said defect, the second sheet in the expanded configuration has a first surface which is adjacent to and conformable to the neck of the defect in a fluid flow obstructing manner relative to said defect and has a second surface that is the reverse of said first surface, said second surface is exposed to the inner surface of said defect and said first sheet additionally functions as a securement member to anchor said second sheet of said device proximal said neck of said defect;
wherein said second sheet is deployed in an expanded configuration inside said vascular defect, and said first sheet is deployed outside of said vascular defect in the form of a semicircular cylinder which is convex to said neck portion of said vascular defect.

2. The device of claim 1 wherein said first sheet, said second sheet, or both further comprise a third material which promotes integration with the vasculature of a patient.

3. The device of claim 2 wherein said third material is coated on, embedded in, or mixed in said material of said first sheet, said second sheet, or both.

4. The device of claim 2 wherein said third material is a biocompatible adhesive.

5. The device of claim 2 wherein said third material comprises at least one member selected from the group consisting of materials which promote healing, materials which promote fibrosis, materials which promote endothelialization, materials which promote tissue growth and mixtures thereof.

6. The device of claim 5 wherein said third material comprises at least one member selected from the group consisting of proteins, drugs, genetic material, cells or cell fragments, processed human or animal tissue, engineered vascular tissue, matrix material from bodily organs, biocompatible polymers, and mixtures thereof.

7. The device of claim 6 wherein said biocompatible polymer is selected from the group consisting of collagen, polysaccharide, fibrin, fibronectin, polylactide, polyglycolide, polycarbonate, polycaprolactone, polyhydroxyalkanoate, poly-p-dioxanone, polyanhydride, any copolymer thereof, and mixtures thereof.

8. The device of claim 2 wherein said third material comprises at least one member selected from the group consisting of antibodies, cytokines, growth factors, enzymes, anticoagulants, hormones, antineoplastic agents, or mixtures thereof.

9. The device of claim 1 further comprising at least one radiopaque material.

10. The device of claim 1 wherein at least one of said first sheet and said second sheet has a surface which promotes integration with said vasculature, said surface comprising at least one material selected from the group consisting of materials which promote healing, materials which promote fibrosis, materials which promote endothelialization, materials which promote tissue growth and mixtures thereof.

11. The device of claim 10 wherein said material is selected from the group consisting of proteins or protein fragments, drugs, genetic material, cells or cell fragments, processed human or animal tissue, engineered vascular tissue, matrix material from bodily organs, and mixtures thereof.

12. A device for the occlusion of a defect in the vasculature, the defect having a neck portion, said device comprising:
a first sheet formed from a first material and having an unexpanded and an expanded configuration, said unexpanded configuration being in the form of a rolled, elongate cylindrical shape having a longitudinal axis and said expanded configuration is a semicircular cylinder; and
a second sheet formed from a second material which is the same as or different from said first material and having an unexpanded configuration in which said second sheet is conformed onto the surface of said rolled, elongate cylindrical shape of said unexpanded first sheet, and an expanded configuration in which said second sheet expands transversely outward from the longitudinal axis of said first sheet to form one of an umbrella-like shape or a semi-spherical shape, said first sheet and said second sheet are connected by a separable connector, each of said first sheet and said second sheet shaped to function as an occlusion member, the second sheet formed from a swellable polymer material and conformable to the neck of the defect in a fluid flow obstructing manner relative to said defect and said first sheet additionally functions as a securement member to anchor said second sheet of said device proximal said neck of said defect.

13. The device of claim 1 wherein said first surface of said second sheet member which is adjacent said neck of said aneurysm bends convexly to said neck of said defect.

14. The device of claim 12 wherein said swellable polymer material is a hydrogel or swellable foam.

15. The device of claim 12 wherein said first sheet comprises a swellable polymer material.

16. The device of claim 1, wherein said first sheet is formed of a rectangular sheet.

17. The device of claim 12, wherein said first sheet is formed of a rectangular sheet.

* * * * *